United States Patent
Oleksy et al.

(10) Patent No.: US 9,446,216 B2
(45) Date of Patent: Sep. 20, 2016

(54) CANNULAR DEVICE AND METHOD OF MANUFACTURE

(75) Inventors: Christopher Alan Oleksy, Maple Grove, MN (US); Roger Warren Brink, Muskegon, MI (US)

(73) Assignee: Medtronic, Inc., Mounds View, MN (US)

( * ) Notice: Subject to any disclaimer, the term of this patent is extended or adjusted under 35 U.S.C. 154(b) by 964 days.

(21) Appl. No.: 13/042,798

(22) Filed: Mar. 8, 2011

(65) Prior Publication Data

US 2012/0095446 A1    Apr. 19, 2012

Related U.S. Application Data

(60) Provisional application No. 61/393,167, filed on Oct. 14, 2010.

(51) Int. Cl.
| | | |
|---|---|---|
| *A61M 25/00* | (2006.01) | |
| *A61L 29/04* | (2006.01) | |
| *A61L 29/06* | (2006.01) | |
| *A61L 29/14* | (2006.01) | |
| *B29C 47/00* | (2006.01) | |
| *B29C 47/88* | (2006.01) | |

(Continued)

(52) U.S. Cl.
CPC ......... *A61M 25/0043* (2013.01); *A61L 29/041* (2013.01); *A61L 29/06* (2013.01); *A61L 29/14* (2013.01); *A61M 25/0009* (2013.01); *A61M 25/0021* (2013.01); *A61M 25/0023* (2013.01); *A61M 2025/0059* (2013.01); *B29C 47/0023* (2013.01); *B29C 47/0026* (2013.01); *B29C 47/8895* (2013.01); *B29C 2947/92704* (2013.01); *B29C 2947/92876* (2013.01); *B29K 2995/0056* (2013.01); *B29L 2023/007* (2013.01); *B29L 2031/7542* (2013.01)

(58) Field of Classification Search
CPC ................... A61M 25/0009; A61M 25/0043; A61M 2025/0059; A61M 25/0021
USPC ................................................. 604/523, 525
See application file for complete search history.

(56) References Cited

U.S. PATENT DOCUMENTS

| | | |
|---|---|---|
| 4,563,180 A | 1/1986 | Jervis et al. |
| 5,045,071 A | 9/1991 | McCormick et al. |
| 5,851,203 A | 12/1998 | Van Muiden |

(Continued)

FOREIGN PATENT DOCUMENTS

| | | |
|---|---|---|
| WO | WO96/26825 | 9/1996 |
| WO | 0076564 A1 | 12/2000 |

OTHER PUBLICATIONS

International Search Report for PCT/US2011/027513 mailed May 9, 2011.

(Continued)

*Primary Examiner* — Emily Schmidt

(57) ABSTRACT

A cannula comprising a polymeric material which is phthalate-free, yet retains flexibility, workability and elongation properties so as to avoid kinking when bent. Also disclosed is a method of manufacturing a cannular device comprising extruding a flexible, biocompatible, phthalate-free polymeric composition through a round die into a tube, pulling the tube through a water bath at a rate established according to a predetermined function, and cutting the tube to for a cannular device, wherein the predetermined function periodically modulates a pulling rate.

22 Claims, 1 Drawing Sheet

(51) Int. Cl.
  *B29L 23/00* (2006.01)
  *B29L 31/00* (2006.01)

(56)     References Cited

U.S. PATENT DOCUMENTS 7,129,224 B1  10/2006  Byun et al.

2001/0051786 A1  12/2001  Davey et al.
2005/0113801 A1  5/2005  Gandras
2009/0012481 A1  1/2009  Davey et al.
2010/0108172 A1  5/2010  Liu et al.

OTHER PUBLICATIONS

EP11832888.9, EP Search Report, mailed Mar. 3, 2014, 11pgs.

CANNULAR DEVICE AND METHOD OF MANUFACTURE

CROSS-REFERENCE TO RELATED APPLICATION

This application claims benefit of copending U.S. Provisional Patent Application No. 61/393,167, filed Oct. 14, 2010, entitled CANNULAR DEVICE AND METHOD OF MANUFACTURE, and commonly assigned to the assignee of the present application, the disclosure of which is incorporated by reference in its entirety herein

BACKGROUND

The present disclosure relates to polymeric tubular conduit for insertion into the body and methods of manufacturing the same. The conduit comprises a polymeric material combinable with other suitable components for cannulation in medical applications.

Cannulation is a process of introducing a cannula into the body of a patient (e.g., body cavity, duct or blood vessel, organ, or the like) for the introduction or removal of fluids (e.g., blood, medications, or air) or devices (e.g., catheter). The cannula may be used for short periods of time (e.g., during surgery) or for extended periods (e.g., extracorporeal membrane oxygenation (ECMO)). For example, surgical procedures related to a patient's heart may require the blood flow through the heart be by-passed in favor of an extracorporeal circulation device (e.g., a heart lung machine). A heart lung machine can be used to circulate and oxygenate blood while the patient's heart is being repaired. The heart lung machine is coupled to the patient's vascular system through specialized conduits called cannulae (plural of cannula). Cannulae adapted to receive blood from the body and transmit the blood to the heart lung machine are called venous cannulae. Cannulae adapted to return blood from the heart lung machine back to the body are called arterial cannulae.

Cannulae were used in human heart bypass surgeries as early as the 1950's. Since then, the overall designs of the most widely used arterial and venous cannula have not changed dramatically. Historically, cannulae are semi-rigid components often made of polyvinyl chloride (PVC) secured by sutures in the patient's arterial and venous structures. When a cannula is made from PVC, plasticizers are often used to provide the PVC, a highly rigid polymer without plasticizers, with the appropriate properties. A plasticizer is an additive that increases a polymer's flexibility, workability, and ability to be elongated. Plasticizers essentially lubricate the polymer chains in a polymer composition so that the intermolecular forces between and along the chains are reduced. This loosening of the intermolecular forces allows the polymer chains to slide across each other more freely.

Most plasticizers are organic compounds with elevated boiling points, low vapor pressures, and poor water solubility. For example, ester phthalates are regularly used because of their particular effectiveness in lubricating polymeric materials. Currently, two commonly used plasticizers are di-2-ethylhexyl phthalate (DEHP) and di-isononyl phthalate (DINP) both of which are phthalates. These plasticizers are routinely used with PVC to make a variety of products. For example, many medical products, toys, and baby products include components comprising PVC and a plasticizer like DEHP. The incorporation of the plasticizers into PVC products provides the composition with the soft, flexible, and supple feel that is associated with these products.

Plasticizers can be compounded with the polymeric materials with which they are used. Most plasticizers do not react to form any chemical bonds with the polymer. Essentially, the plasticizer is dissolved within the polymeric material because of the favorable physical interactions between the polymer and the plasticizer. The favorable physical interactions typically prevent the plasticizer from leaching out of the polymer. While plasticizers are typically not water soluble, they are soluble in non-polar solvents and are known to be slightly soluble in blood and other bodily fluids. Accordingly, in a cannula manufactured with a plasticizer an amount of plasticizer may be leached out in vivo and become dissolved in bodily fluids. For example, a publication by Peck and Albro, *Environmental Health Perspectives* Vol. 45, pp. 11-17, 1982, found that DEHP plasticizer from a PVC/DEHP blood bag accumulate in plasma during 4° C. liquid whole blood storage at a rate of approximately 1 mg/unit/day. There has been extensive research and debate surrounding the toxicological impact of DEHP in biological fluid. The results have been inconsistent and there is not a clear answer as to whether and to what extent such plasticizers may be a health risk to patients. It would be desirable to produce a cannular device which is free of plasticizers yet will provide the desired properties of flexibility, workability and ability to be elongated.

SUMMARY

The present disclosure provides in one exemplary embodiment a polymeric tubular conduit for use in patients and methods of manufacturing the same. The conduit comprises a polymeric material combinable with other suitable components for cannulation in medical applications.

In one illustrative embodiment, a cannular device of the present disclosure comprises a polymeric conduit having an inner lumen, a proximal end having a proximal opening, and a distal end having a distal opening, arranged so that the inner lumen extends from the proximal opening to the distal opening. The polymeric conduit comprises a biocompatible polymeric composition free of plasticizers, for example (but not by way of limitation) free of di-2-ethylhexyl phthalate (DEHP), DINP or other phthalate-based compound. The polymeric conduit may be arranged to have a circular, elliptical, oval or other cross-section shape defining an inner diameter and an outer diameter. The cross-section diameter may diminish in size from the proximal end to the distal end from a first inner diameter and first outer diameter to a second inner diameter and a second outer diameter. The first inner diameter may be larger than the second inner diameter and the first outer diameter may be larger than the second outer diameter. The polymeric conduit is adapted to resist kinking so that the inner lumen remains free from obstruction when tested according to a standard 180° bend test. The inner diameter of the polymeric conduit may diminish according to a first continuous function, the function providing a gradual diminution of diameter from the proximal end to the distal end. The outer diameter may diminish according to a second continuous function, the function providing a gradual diminution of size from the proximal end to the distal end.

In one illustrative embodiment, a method of manufacturing a cannular device in accordance with the present disclosure comprises extruding a flexible, biocompatible, phthalate-free polymeric composition through a round die into a tube, pulling the tube through a water bath at a rate established according to a predetermined function, and cutting the tube to form the cannular device. The predetermined function periodically modulates a pulling rate. The predetermined function may also provide periods of time in which the pulling rate increases from a minimal pulling rate to a maximal pulling and periods of time in which the pulling rate decreases from a maximal pulling rate to a minimal pulling rate. The modulation of the pulling rate according to this function provides the tube with an oscillating cross-sectional diameter changing with time. The predetermined function may also provide periods in which the pulling rates are not modulated. In one illustrative embodiment, the periods in which the pulling rates are not modulated are interposed between periods in which the pulling rates are modulated.

BRIEF DESCRIPTION OF DRAWINGS

So the manner in which the above-recited features of the present disclosure can be understood in detail, a more particular description of the present disclosure may be had by reference to embodiments, which are illustrated in the appended drawings. It is to be noted, however, that the appended drawings illustrate only typical embodiments encompassed within the scope of the present disclosure, and, therefore, are not to be considered limiting, for the present invention may admit to other equally of effective embodiments, wherein.

DETAILED DESCRIPTION

Figure 1:
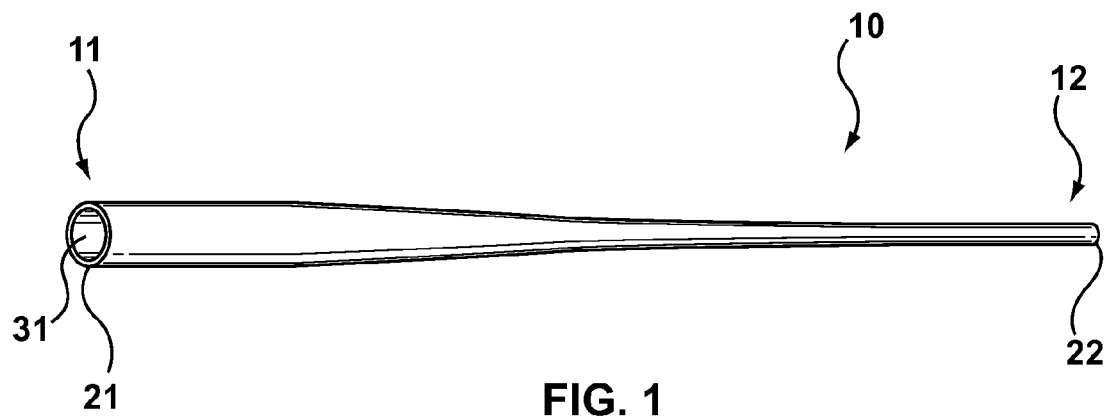
FIG. 1 is a perspective view of a first exemplary embodiment of cannular device having a proximal end and proximal opening, a distal end and distal opening, and an interior conduit defined between the proximal opening and the distal opening.
Figure 2:
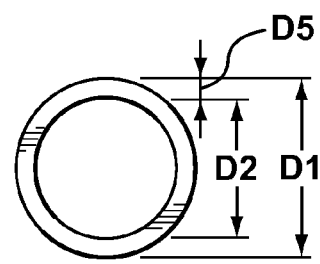
FIG. 2 is an end view shown in FIG. 1 of the proximal opening showing that at the proximal opening the conduit has a first outer diameter, a first inner diameter, and a first wall thickness.
Figure 3:
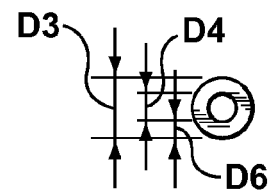
FIG. 3 is an end view of the distal opening shown in FIG. 1 showing that at the distal opening the conduit has a second outer diameter, a second inner diameter, and a second wall thickness.

Referring now to FIG. 1, shown is a perspective view of a first exemplary embodiment of a cannular device 10 having a proximal end 11 and proximal opening 21, a distal end 12 and a distal opening 22, and an interior lumen 31 defined therein between proximal opening 21 and distal opening 22. FIG. 2 is an end view of proximal opening 21 showing that at the proximal opening the conduit has a first outer diameter D1, a first inner diameter D2, and a first wall thickness D5. FIG. 3 is an end view of distal opening 22 showing that at distal opening 22 the conduit has a second outer diameter D3, a second inner diameter D4, and a second wall thickness D6.

The use of cannular devices in cardiac surgery makes particular cannular designs preferable over others. For example, cannulae designs that maximize fluid flow are more desirable than those with lesser flow capabilities. While maximizing flow is desirable, surgeons must balance the need for flow against the trauma that a given cannular device may impart upon the recipient body. Thus, a desirable cannula design generally includes the largest internal diameter cannula (for flow) that has an outer diameter that can be atraumatically inserted into the body. Thus, maximum distal external diameter (e.g., second outer diameter D3) is limited to the size of the bodily member in which the cannular device is inserted. For example, a cannular device having an external diameter larger than the blood vessel could not be inserted therein. Furthermore, there are standard connection sizes for the proximal opening (first inner diameter D2) that makes certain sizes desirable. For example, many connectors are sized at $3/16$, $1/4$, $3/8$, $4/10$ inches, etc.

In addition to the basic dimensional size requirements of a cannular device, the shape of the cannular device influences the turbulence of flow of fluid through the device. Abrupt changes in the shape or cross-sectional area of a cannular device may cause turbulent flow characteristics. An abrupt expansion, contraction, or change in flow direction may have an adverse affect on the fluid being transmitted. Thus, some device geometries may be favorable to others due to their internal flow characteristics during use.

For a cannular device to be selected by a surgeon, there are certain dimensional characteristics that are desirable. For example, the proximal opening should facilitate the use of various connectors or enable the cannular device to be directly connected to extracorporeal tubing. The distal opening should facilitate the use of various tips or have dimensions and shapes suitable for direct insertion into the body. FIG. 1 is an exemplary cannular device shape that is known to possess these desirable dimensional characteristics. With respect to cannular device 10, it includes a gradually tapered diameter that is free of abrupt size changes.

In one illustrative embodiment, a cannular device of the present disclosure comprises a polymeric conduit defining an inner lumen, a proximal end having a proximal opening, and a distal end having a distal opening arranged so that the inner lumen extends from the proximal opening to the distal opening. The polymeric conduit comprises a biocompatible polymeric composition free of plasticizers, for example free of di-2-ethylhexyl phthalate. Cannular devices manufactured with polyvinyl chloride (PVC) contain substantial concentrations of plasticizers such as di-2-ethylhexyl phthalate. In one embodiment, the cannular devices of the present disclosure are not manufactured using PVC or plasticizers. In another embodiment, the cannular devices of the present disclosure are not manufactured with phthalates.

In one illustrative embodiment, a cannular device includes a polymeric composition comprising a thermoplastic elastomer (TPE). One aspect of the present disclosure is that it was discovered that thermoplastic elastomers may be used in place of PVC and plasticizers. As used herein, thermoplastic elastamers means polymeric materials having the flexibility properties like rubbers, strength properties like plastics, and processability properties like thermoplastics. Illustratively, a thermoplastic elastomer may be sufficiently elastomeric to return to its original shape (or nearly do so) after moderate elongation. Further illustratively, a thermoplastic elastomer may be sufficiently thermoplastic to enable melt processability while substantially avoiding creep at room temperature. Thus, a thermoplastic elastomer may be partially characterized by the absence of significant creep while having thermoplastic and elastomeric properties.

Thermoplastic elastomers are distinct from thermosetting elastomers because thermosetting materials (generally) become rigid upon processing (though there are some elastomers which have properties of both classes). A thermosetting elastomer would generally not be useful within the scope of the present disclosure because it would loose its flexibility upon cooling after exposure to processing temperatures. In contrast, thermoplastic materials are considered easy to use in manufacturing because they maintain their properties through a thermo-forming process. For example, a thermoplastic material would have similar properties before and after a manufacturing procedure such as injection molding. The difference in a thermoplastic elastomer and a thermosetting elastomer can be traced to the different chemical interactions that provide the differing physical properties. For thermosetting elastomers, covalent crosslinks may form as the result of a processing step (e.g., vulcanization). The formation of covalent crosslinks permanently changes the chemical structure of the polymer so that material's properties change substantially. Thermoplastic elastomers include weaker crosslinking moieties that rely on dipole-dipole interactions or hydrogen bonding. During a processing step, these weak crosslinks lose the ability to restrict the shape of the material due to its thermal energy (i.e., the material melts), but upon cooling, the weak bonds reform and again have sufficient strength to keep the material's shape constant (i.e., solidification).

The term "thermoplastic elastomer" covers a broad range of chemical compositions with dramatically different chemical and physical properties. Representative thermoplastic elastomers include, but are not limited to, styrenic block copolymers, polyolefin blends, elastomeric alloys, thermoplastic polyurethanes, thermoplastic copolyesters and thermoplastic polyamides. There are a number of chemical manufacturers providing a wide range of TPE products under various trade names, for example: EXELAST SX® (Shin-Etsu Polymer Europe B.V.), STYROFLEX®, ELASTOLLAN® (BASF & Elastogran), PEARLTHANE® (Merquinsa), DESMOPAN® (Bayer), ESTANE® (Lubrizol), IROGRAN® (Huntsman), PELLETHANE®, ENGAGED (Dow Chemical), PEBAX®, ARNITEL®, SARLINK® (DSM), HYTREL (Du Pont), DRYFLEX®, MEDIPRENE® (ELASTO, a Hexpol Company), VERSAFLEX® (PolyOne GLS), SANTOPRENE® (ExxonMobil Chemical), KRATON® (Kraton Polymers), and PEBAX® (Arkema).

There are virtually limitless TPE compositions and blends thereof that may or may not provide useful properties within the scope of the present disclosure. One aspect of the present disclosure is that the attributes of preferred compositions are set forth so that one skilled in the art may appreciate those compositions useful for applications as described herein.

In one illustrative embodiment, a thermoplastic elastomer has a Durometer hardness (Shore A, 10 sec) as determined according to ASTM D2240 of about 45 to about 85. In one embodiment, the thermoplastic elastomer has a Durometer hardness of about 55 to about 75. In another embodiment, the thermoplastic elastomer has a Durometer hardness of about 60 to about 70. In yet another embodiment, the thermoplastic elastomer has a Durometer hardness of about 65. Another aspect of the present disclosure is that it was discovered that the physical dimensions of a particular cannular device may require a TPE with having a particular Durometer hardnesses. Illustratively, a TPE having a higher hardness was determined to be better suited for a cannular device having a small diameter and thin walls. In contrast, it was determined that a TPE having lower hardness provided enhanced properties in those cannular devices having larger diameters and thicker walls.

In one illustrative embodiment, the thermoplastic elastomer has a density as determined according to ASTM D792 of about 0.80 g/cm$^3$ to about 0.95 g/cm$^3$. In one embodiment, the thermoplastic elastomer has a density of about 0.83 g/cm$^3$ to about 0.92 g/cm$^3$. In another embodiment, the thermoplastic elastomer has a density of about 0.86 g/cm$^3$ to about 0.89 g/cm$^3$. In yet another embodiment, the thermoplastic elastomer has a density of about 0.88 g/cm$^3$.

In one illustrative embodiment, the thermoplastic elastomer has a tensile stress (100% Strain, 73° F.) of about 100 psi to about 500 psi as determined according to ASTM D421. In one embodiment, the thermoplastic elastomer has a tensile stress (100% Strain, 73° F.) of about 150 psi to about 400 psi. In another embodiment, the thermoplastic elastomer has a tensile stress (100% Strain, 73° F.) of about 200 psi to about 350 psi. In yet embodiment, the thermoplastic elastomer has a tensile stress (100% Strain, 73° F.) of about 280 psi.

In one illustrative embodiment, the thermoplastic elastomer has a tensile strength of about 600 psi to about 1800 psi and an elongation to break of about 300% to about 900% as determined according to ASTM D421. In one embodiment, the thermoplastic elastomer has a tensile strength of about 900 psi to about 1500 psi and an elongation to break of about 450% to 750%. In another embodiment, the thermoplastic elastomer has a tensile strength of about 1200 psi and an elongation to break of about 650%.

In one illustrative embodiment, the thermoplastic elastomer is selected and adapted so that the surface (generally exterior) of the cannular device accepts ink upon printing. Thermoplastic elastomers vary significantly on their receptiveness to being printed. In many of the medical applications that a cannular device of the present disclosure is used, the cannular device should include markings for identification or for the assistance of the surgeon during use. Accordingly, the combination of the TPE, as disclosed herein and method of manufacture provide a cannular device that accepts ink upon printing.

In one illustrative embodiment, the thermoplastic elastomer can be bump extruded at a melt temperature of about 150° C. to about 250° C. and a die temperature of about 140° C. to about 240° C. In one embodiment, the thermoplastic elastomer can be bump extruded at a melt temperature of about 170° C. to about 220° C. and a die temperature of about 160° C. to about 210° C. In another embodiment, the thermoplastic elastomer can be bump extruded at a melt temperature of about 180° C. to about 205° C. and a die temperature of about 170° C. to about 200° C.

In one illustrative embodiment, upon extruding the thermoplastic elastomer, it is sufficiently clear so that the fluids passing through the lumen can be adequately observed. The clarity of the cannular device can be tested by visually inspecting high contrast markings through the cannular device. A failing cannular device inhibits the visual determination of the high contrast markings. A passing device allows for the visual determination of the high contrast markings. As a standard reference material, a cannular device manufactured using PVC and plasticizers can be used for comparison to the devices described herein. One aspect of the present disclosure is that the combination of the TPE, as disclosed herein, the cannular design (e.g., thickness of walls, extent of taper, length, diameters, taper rates, and smoothness), and method of manufacture provide a sufficiently clear cannula for use in medical procedures.

In one illustrative embodiment, the cannular device includes a polymeric conduit that is arranged to have a circular cross-section defining an inner diameter and an outer diameter, the circular cross-section may diminish in size from the proximal end to the distal end from a first inner diameter and first outer diameter to a second inner diameter and a second outer diameter. The first inner diameter is larger than the second inner diameter and the first outer diameter is larger than the second outer diameter. Illustratively, the shape of the cannular device is tapered from the proximal end to the distal end. In one illustrative embodiment, the inner diameter of the proximal end is less than 1 inch. In one embodiment, the inner diameter of the proximal end is less than or equal to about 0.75 inches. In another embodiment, the inner diameter of the proximal end is about 0.4 inches. In another embodiment, the inner diameter of the proximal end is about 0.375 inches. In another embodiment, the inner diameter of the proximal end is about 0.375 inches. In another embodiment, the inner diameter of the proximal end is between about 0.1 inches about 0.25 inches.

In one illustrative embodiment, the inner diameter of the distal end is less than 0.75 inches. In one embodiment, the inner diameter of the distal end is less than about 0.5 inches. In another embodiment, the inner diameter of the distal end is about 0.25 inches. In another embodiment, the inner diameter of the distal end is about 0.15 inches. In another embodiment, the inner diameter of the distal end is between about 0.15 inches about 0.25 inches. In another embodiment, the inner diameter of the distal end is between about 0.15 inches about 0.05 inches.

In further one illustrative embodiment, the wall thickness at the distal end is between about 0.2 inches and 0.005 inches. In one embodiment, the wall thickness at the distal end is between about 0.1 and 0.01 inches. In another embodiment, the wall thickness at the distal end is between about 0.09 and 0.05 inches. In one illustrative embodiment, the "average wall thickness change per inch length to diameter change per inch length" ratio was determined to influence kink resistance. In one embodiment, the average wall thickness change per inch length to diameter change per inch length ratio is between about 3 and about 70. In another embodiment, the average wall thickness change per inch length to diameter change per inch length ratio is between about 6 and about 35. In another embodiment, the average wall thickness change per inch length to diameter change per inch length ratio is greater than about 7.5.

Figure 4:
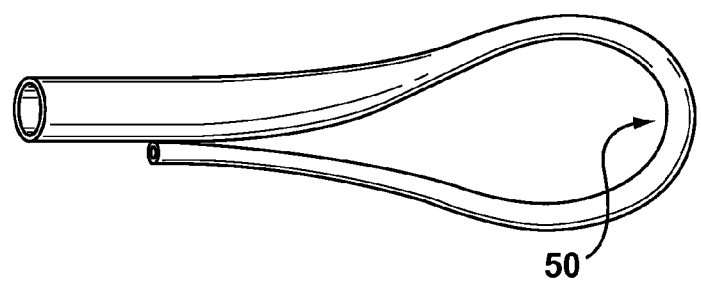
FIG. 4 is a perspective view of the device of FIG. 1 subjected to a 180° bend test showing that the device does not kink when so tested.

One aspect of the present disclosure is that the polymeric conduit is adapted to provide means for resisting kinking so that the inner lumen remains free from obstruction when tested according to the 180° bend test. Referring now to FIG. 4, shown is a perspective view of the device of FIG. 1 subjected to a 180° bend test showing that the device does not kink when so tested. In particular, the 180° bend test involves bending the cannular device so that the distal end and the proximal end are in contact and oriented in a parallel fashion as shown. A cannular device failing the 180° bend test would exhibit a crease or kink at a location 50 in roughly the middle of the device. A cannular device passing the 180° bend test does not exhibit any kink or crease over the entire device. One aspect of the present disclosure is that the combination of the TPE, as disclosed herein, the cannular design (e.g., thickness of walls, extent of taper, length, diameters, taper rates, and smoothness), and method of manufacture provide a robust cannular device that passes the 180° bend test.

Figure 5:
FIG. 5 is a perspective view of a prior art device made through a dip-molding process showing that the device includes a wire-wound body to avoid kinking.

Referring now to FIG. 5, shown is a perspective view of a prior art device made through a dip-molding process showing that the device includes a wirewound body to avoid kinking. In one illustrative embodiment of the present disclosure the polymeric conduit is wire-free. One aspect of the present disclosure is that the combination of the TPE, as disclosed herein, the cannular design (e.g., thickness of walls, extent of taper, length, diameters, taper rates, and smoothness), and method of manufacture provide a robust cannular device that passes the 180° bend test without the inclusion of wire in the device.

Another aspect of the present disclosure is that the polymer composition of the conduit is adapted to recover to full patency to cause the inner lumen to remain free from obstruction after being clamped to complete closure. Use of the cannular device in medical procedures may require that the device be clamped so as to stop flow of a fluid through the lumen of the device. Clamping of the device exerts significant pressures on the walls of the device, but recovery to full patency is enabled through the compositions and described herein. A cannular device failing the clamp test would either be too stiff to properly clamp, be too "sticky" and one wall would adhere to the opposite wall thus failing to fully recover its circular cross-section, be too brittle and crack, or be insufficiently elastic so that the deformation from the clamp becomes permanent. A cannular device passing the clamp test would recover full patency (return to generally the same shape it was prior to clamping). One aspect of the present disclosure is that the combination of the TPE, as disclosed herein, the cannular design (e.g., thickness of walls, extent of taper, length, diameters, taper rates, and smoothness), and method of manufacture provide a robust cannular device that passes the clamp test.

In one illustrative embodiment, the inner diameter of the polymeric conduit diminishes according to a first continuous function, the function providing a gradual diminution of diameter from the proximal end to the distal end. In one embodiment, the outer diameter diminishes according to a second continuous function, the function providing a gradual diminution of size from the proximal end to the distal end. The first continuous function and the second continuous function may or may not be equivalent so that the wall thickness at the distal end and the proximal end may or may not be the same. In one embodiment, the first continuous function provides a diminution of diameter of about 0.001 to about 0.05 inch per linear inch. In another embodiment, the first continuous function provides a diminution of diameter of about 0.003 to about 0.03 inch per linear inch. In yet another embodiment, the first continuous function provides a diminution of diameter of about 0.003 to about 0.01 inch per linear inch. In one embodiment, the second continuous function provides a diminution of diameter of about 0.0001 to about 0.05 inch per linear inch. In yet another embodiment, the first continuous function provides a diminution of diameter of about 0.0001 to about 0.03 inch per linear inch. In another embodiment, the first continuous function provides a diminution of diameter of about 0.0001 to about 0.01 inch per linear inch. In another embodiment, the first inner diameter and the first outer diameter define a first thickness for the polymer conduit at the proximal end opening and the second inner diameter and the second outer diameter define a second thickness for the polymer conduit at the distal end, wherein the second thickness is about 50 to about 95% of the first thickness.

In one illustrative embodiment, the change in wall thickness from the proximal opening to the distal opening decreases according to a third continuous function, the third continuous function providing gradual step-less thickness diminution from the proximal end opening to the distal opening. In one embodiment, the third continuous function provides a diminution of thickness of about 0.00005 to about 0.005 inch per linear inch. In another embodiment, the third continuous function provides a diminution of thickness of about 0.0001 to about 0.003 inch per linear inch. In another embodiment, the third continuous function provides a diminution of thickness of about 0.001 to about 0.002 inch per linear inch.

In one illustrative embodiment, the polymeric conduit is adapted to provide means for bonding with adhesives to cause tips and connectors attached thereto with adhesive to remain affixed. One aspect of the disclosure is that the cannular device shown in FIG. 1 may be considered a component of a finished medical device. As such, other components may be combined with the cannular device shown to produce a cannular device of increased complexity. The other components may be configured with the illustrated cannular device through the use of solvent setting, melt fusing, or adhesives. One aspect of the present disclosure is that the combination of the TPE, as disclosed herein, the cannular design (e.g., thickness of walls, extent of taper, length, diameters, taper rates, and smoothness), and method of manufacture provide properties that enable the manufacture of cannular devices of greater complexity. In further one illustrative embodiment, the polymeric conduit is adapted to provide means for maintaining color to cause device to retain un-yellowed color during accelerated aging.

In one illustrative embodiment, a method of manufacturing a cannular device in accordance with the present disclosure comprises extruding a flexible, biocompatible, phthalate-free polymeric composition through a round die into a tube, pulling the tube through a water bath at a rate established according to a predetermined function, and cutting the tube to form the cannular device. The predetermined function periodically modulates a pulling rate. The predetermined function may also provide periods of time in which the pulling rate increases from a minimal pulling rate to a maximal pulling and periods of time in which the pulling rate decreases from a maximal pulling rate to a minimal pulling rate. The modulation of the pulling rate according to this function provides the tube with an oscillating cross-sectional diameter changing with time. The predetermined function may also provide periods in which the pulling rates are not modulated. In one illustrative embodiment, the periods in which the pulling rates are not modulated are interposed between periods in which the pulling rates are modulated.

Table 1 below depicts comparative test data between cannulae in accordance with embodiments of the present disclosure, and cannulae manufactured in accordance with conventional compositions. The flow test were conducted with BioPump using water. Cannulae were connected in series with pressure box plumbed into proximal end with the distal end exhausting into tray. Comparative Examples A, B, and C are made with phthalate containing PVC having a design as shown in FIG. 5. Examples 1, 2, and 3, have a design like that shown in FIG. 1 and are made from a thermoplastic elastomer (GLS VERSAFLEX® HC MT222). The Examples 1, 2, and 3 were designed to have matching dimensions to Comparative Examples A, B, and C. In particular, Comparative Example A and Example 1 are 14 in (35.6 cm) in overall length, having a ¼ in (0.64 cm) diameter proximal opening (12 Fr (4.0 mm)). Comparative Example B and Example 2 are 14 in (35.6 cm) in overall length, having a ¼ in (0.64 cm) diameter proximal opening (20 Fr (6.7 mm)). Comparative Example C and Example 3 are 8.5 in (21.6 cm) in overall length, having a ⅜ in (0.95 cm) diameter proximal opening (20 Fr (6.7 mm)).

In addition to the flow test data shown in Table 1, the following specifications were considered: clarity-comparative and exemplary devices equivalent, waviness-exemplary devices acceptable, proximal end squareness-exemplary devices all within +/−3°, room temperature kink-exemplary devices remain kink-free with 180° bend, 37° C. kink-exemplary devices remain kink-free with 180° bend, room temperature clamp-exemplary devices returned to full patency, 37° C. clamp-exemplary devices returned to full patency, ink adhesion-exemplary devices acceptable, adhesive bonding-exemplary devices acceptable, and accelerated aging-exemplary devices showed acceptable performance at 3 years.

TABLE 1

| A | | 1 | | |
|---|---|---|---|---|
| RPM | Press. | RPM | Press. | Δ Press. |
| 500 | 9 | 500 | 9 | 0 |
| 1000 | 39 | 1000 | 38 | 1 |
| 1500 | 87 | 1510 | 86 | 1 |
| 2000 | 150 | 2010 | 150 | 0 |
| B | | 2 | | |
| RPM | Press. | RPM | Press. | Δ Press. |
| 510 | 4 | 510 | 4 | 0 |
| 1000 | 19 | 1000 | 20 | −1 |
| 1540 | 50 | 1510 | 49 | 1 |
| 2020 | 83 | 2030 | 87 | −4 |
| 2530 | 130 | 2520 | 132 | −2 |
| C | | 3 | | |
| RPM | Press. | RPM | Press. | Δ Press. |
| 530 | 4 | 530 | 4 | 0 |
| 1010 | 17 | 1000 | 17 | 0 |
| 1530 | 42 | 1520 | 42 | 0 |
| 2020 | 72 | 2030 | 78 | −6 |

It is to be understood that the cannular device and method of producing the device can be adapted for other uses and applications, such as noninvasive medical devices, drinking straws, intra venous tubes, and the like. All patents, applications, and publications referred to herein are incorporated by reference in their entirety. Although only a number of exemplary embodiments have been described in detail above, those skilled in the art will readily appreciate that many modifications are possible in the exemplary embodiments without materially departing from the novel teachings and advantages. Accordingly, all such modifications are intended to be included within the scope of this disclosure as defined in the following claims

The invention claimed is:
1. A cannular device, comprising:
  a polymeric conduit defining an inner lumen, a proximal end having a proximal opening, and a distal end having a distal opening arranged so that the inner lumen extends from the proximal opening to the distal opening,
  wherein the polymeric conduit comprises a biocompatible polymeric composition free of phthalate containing materials,
  wherein the polymeric conduit is arranged to have a circular cross-section defining an inner diameter and an outer diameter, the circular cross-section diminishing in size from the proximal end to the distal end from a first inner diameter and first outer diameter to a second inner diameter and a second outer diameter, the first inner diameter being larger than the second inner diameter and the first outer diameter being larger than the second outer diameter, wherein the polymeric conduit is adapted to provide means for resisting kinking so that the inner lumen remains free from obstruction when tested according to the 180° bend test, wherein the inner diameter diminishes according to a first continuous function, the function providing a gradual diminution of diameter from the proximal end to the distal end, and wherein the outer diameter diminishing according to a second continuous function, the function providing a gradual diminution of size from the proximal end to the distal end.

2. The device of claim 1, wherein the first continuous function provides a diminution of diameter of about 0.001 to about 0.05 inch per linear inch.

3. The device of claim 1, wherein the first continuous function provides a diminution of diameter of about 0.003 to about 0.03 inch per linear inch.

4. The device of claim 1, wherein the first continuous function provides a diminution of diameter of about 0.003 to about 0.01 inch per linear inch.

5. The device of claim 1, wherein the second continuous function provides a diminution of diameter of about 0.0001 to about 0.05 inch per linear inch.

6. The device of claim 1, wherein the first continuous function provides a diminution of diameter of about 0.0001 to about 0.03 inch per linear inch.

7. The device of claim 1, wherein the first continuous function provides a diminution of diameter of about 0.0001 to about 0.01 inch per linear inch.

8. The device of claim 1, wherein the first inner diameter and the first outer diameter define a first thickness for the polymer conduit at the proximal end opening and the second inner diameter and the second outer diameter define a second thickness for the polymer conduit at the distal end, wherein the second thickness is about 50 to about 95% of the first thickness.

9. The device of claim 3, wherein the change in thickness from the proximal opening to the distal opening decreases according to a third continuous function, the third continuous function providing gradual step-less thickness diminution from the proximal end opening to the distal opening.

10. The device of claim 9, wherein the third continuous function provides a diminution of thickness of about 0.00005 to about 0.005 inch per linear inch.

11. The device of claim 9, wherein the third continuous function provides a diminution of thickness of about 0.0001 to about 0.003 inch per linear inch.

12. The device of claim 9, wherein the third continuous function provides a diminution of thickness of about 0.001 to about 0.002 inch per linear inch.

13. The device of claim 1, wherein the polymeric composition is free of phthalates.

14. The device of claim 13, wherein the polymeric composition is free of plasticizers.

15. The device of claim 1, wherein the polymeric conduit is wire-free.

16. The device of claim 1, wherein the polymeric composition comprises a thermoplastic elastomer.

17. The device of claim 16, wherein the Shore A hardness of the thermoplastic elastomer is in a range from about 45 to about 85.

18. The device of claim 16, wherein the Shore A hardness of the thermoplastic elastomer is in a range from about 55 to about 75.

19. The device of claim 1, wherein the polymeric conduit adapted to further provide means for recovering to full patency to cause the inner lumen to remain free from obstruction after being clamped to complete closure.

20. The device of claim 1, wherein the polymeric conduit adapted to further provide means for accepting ink to cause ink introduced to the conduit to remain in a location matching that of original printing.

21. The device of claim 1, wherein the polymeric conduit is configured to allow bonding with an adhesive to a tip or connector.

22. The device of claim 1, wherein the polymeric conduit is configured to retain an un-yellowed color during accelerated aging.

* * * * *

UNITED STATES PATENT AND TRADEMARK OFFICE
CERTIFICATE OF CORRECTION

PATENT NO. : 9,446,216 B2  
APPLICATION NO. : 13/042798  
DATED : September 20, 2016  
INVENTOR(S) : Oleksy et al.

Page 1 of 1

It is certified that error appears in the above-identified patent and that said Letters Patent is hereby corrected as shown below:

In the Claims

In Claim 9, Line 41, "The device of claim 3, wherein...." should read -- "The device of claim 8, wherein...." --

Signed and Sealed this  
Twentieth Day of June, 2017

Joseph Matal  
*Performing the Functions and Duties of the*  
*Under Secretary of Commerce for Intellectual Property and*  
*Director of the United States Patent and Trademark Office*